US00PP28737P2

(12) United States Plant Patent
Ault

(10) Patent No.: US PP28,737 P2
(45) Date of Patent: Dec. 5, 2017

(54) ***PHLOX* PLANT NAMED 'EARLY BIRD'**

(50) Latin Name: ***Phlox* hybrid**
Varietal Denomination: Early Bird

(71) Applicant: James Robert Ault, Libertyville, IL (US)

(72) Inventor: James Robert Ault, Libertyville, IL (US)

(73) Assignee: CHICAGOLAND GROWS, INC., Glencoe, IL (US)

( * ) Notice: Subject to any disclaimer, the term of this patent is extended or adjusted under 35 U.S.C. 154(b) by 0 days.

(21) Appl. No.: 15/330,017

(22) Filed: Jul. 26, 2016

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — Penny J. Aguirre

(57) ABSTRACT

A new cultivar of *Phlox* plant named, 'Early Bird', that is characterized by its early bloom period that begins in mid-April, peaks in late April, and lasts four to five weeks, its large, overlapping, conspicuous striae that are deep purplish red in color, its flowers that are deep purplish pink in color, and its flowers that cover 100% of the plant at peak bloom.

2 Drawing Sheets

Botanical classification: *Phlox* hybrid.
Cultivar designation: 'Early Bird'.

BACKGROUND OF THE INVENTION

The present invention relates to a new and distinct cultivar of *Phlox* plant, botanically known as *Phlox* 'Early Bird' and will be referred to hereafter by its cultivar name, 'Early Bird'. The new cultivar represents a new moss *phlox*, a herbaceous perennial grown for landscape use.

The new invention arose from an ongoing controlled breeding program conducted by the Inventor in Glencoe, Ill. The objectives of the breeding program are to develop improved cultivars of interspecific *Phlox* hybrids with novel ornamental traits such as unique flower colors, plant habits, flower fragrance and adaptability to garden conditions in the upper Midwest (U.S.D.A. Zone 5) and similar climates.

'Early Bird' was discovered by the Inventor as a chance seedling growing in his nursery in March of 2012. The new cultivar was found growing in a trial garden located nearby 17 proprietary unnamed cultivars of *Phlox*, thus the exact parentage is unknown.

Asexual propagation of the new cultivar was first accomplished by shoot tip cuttings by the Inventor in May of 2012 in Glencoe, Ill. Asexual propagation by shoot tip cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Early Bird' as a unique cultivar of *Phlox*.

1. 'Early Bird' exhibits an early bloom period that begins in mid-April, peaks in late April, and lasts four to five weeks.
2. 'Early Bird' exhibits petals with large, overlapping, conspicuous striae that are deep purplish red in color.

3. 'Early Bird' exhibits flowers that are deep purplish pink in color.
4. 'Early Bird' exhibits flowers that cover 100% of the plant at peak bloom.

'Early Bird' can be most closely compared to the *Phlox subulata* cultivars 'Crimson Beauty' (not patented) and 'Scarlet Flame' (not patented). 'Crimson Beauty' is similar to 'Early Bird' in flower color and in having conspicuous deep purplish red petal striae. 'Crimson Beauty' differs from 'Early Bird' in having a later commencing bloom period, in having petal striae that are smaller in size and not overlapping, and in having foliage that is larger in size. 'Scarlet Flame' is similar to 'Early Bird' in having conspicuous deep purplish red petal striae. 'Scarlet Flame' differs from 'Early Bird' in having a later commencing bloom period, in having flowers with irregularly shaped petals, in having flowers that are smaller in size, in having a more vigorous growth rate, and in having a less uniform growth habit that is both upright and spreading.

BRIEF DESCRIPTION OF THE DRAWINGS

The accompanying colored photographs illustrate the overall appearance and distinct characteristics of the new *Phlox*. The photographs were taken of three year-old plants of 'Early Bird' as grown outdoors in a trail garden in Glencoe, Ill.

The photograph in FIG. 1 provides a top view of 'Early Bird' illustrating the plant in bloom.

Figure 1:
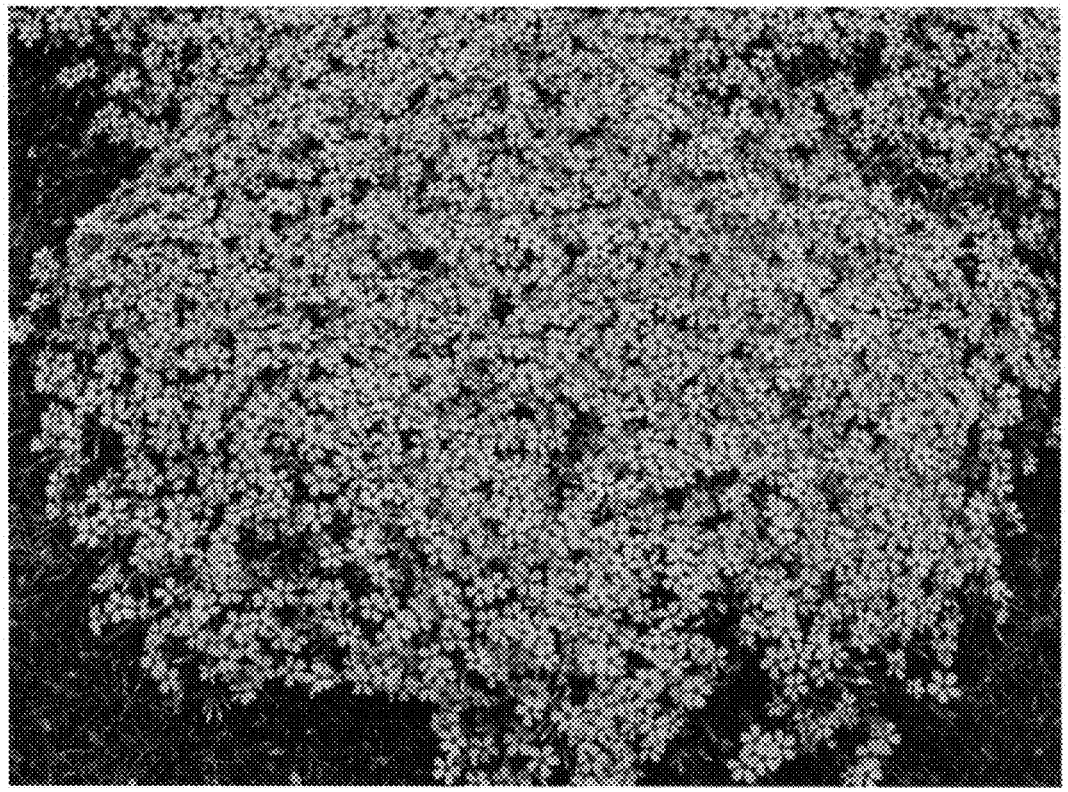
Figure 2:
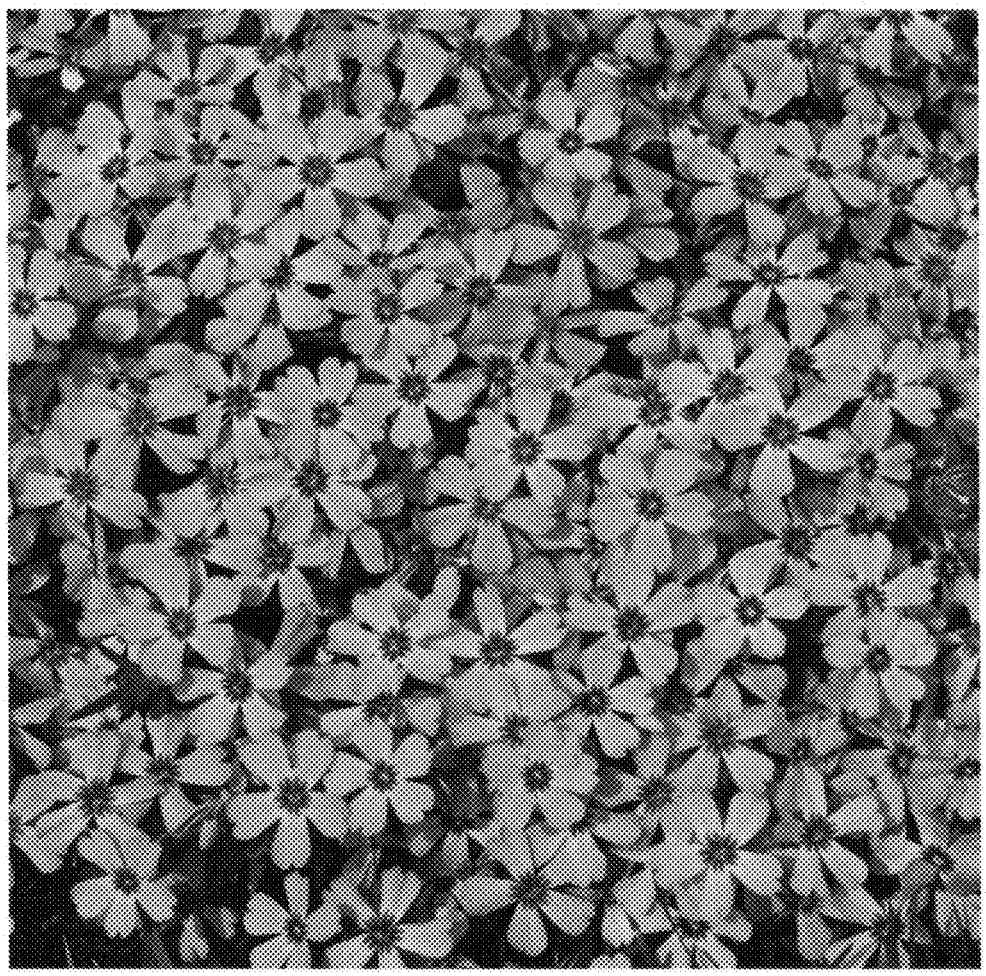

The photograph in FIG. 2 provides a close-up view of the flowers of 'Early Bird'.

The colors in the photographs are as close as possible with the photographic and printing technology utilized and the color values cited in the Detailed Botanical Description accurately describe the colors of the new *Phlox*.

DETAILED BOTANICAL DESCRIPTION OF THE PLANT

The following is a detailed description of three year-old plants of the new cultivar as grown outdoors in a trial garden in Glencoe, Ill. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Blooms for four to five weeks from mid-April to mid-May in northern Illinois.

*Plant type*.—Herbaceous perennial.

*Plant habit*.—Low spreading mound.

*Height and spread*.—An average of 14 cm in height and 49 cm in width, 24 cm descending length.

*Hardiness*.—At least hardy in U.S.D.A. Zones 4 to 8.

*Diseases and pests*.—Resistance to powdery mildew (caused by *Erysiphe cichoracearum*) has been observed.

*Propagation*.—Shoot tip cuttings.

*Root development*.—Shoot tip cuttings will root under mist in 4 to 5 weeks in late spring to early summer, rooted cuttings will fully fill a 2.5 inch pot with roots in 3 to 4 months, and when tranplanted in fall and overwintered in a 4-inch pot, they will bloom the following spring.

*Growth rate*.—Vigorous for a moss *Phlox*.

*Root description*.—Fibrous and NN155C in color.

Stem description:

*Stem size*.—An average of 24 cm in length and 2 mm in width.

*Stem shape*.—Rounded.

*Stem strength*.—Moderately strong and flexible.

*Stem color*.—Young main stems; 157A, flushed with 184A, mature stems; 161A.

*Stem surface*.—Young stems; smooth, very slightly glossy, and densely covered with wooly hairs about 1 mm in length, matching surface color, mature stems; slightly glossy and dry and paper like.

*Stem aspect*.—Held horizontally to descending, drooping and falling downward.

*Internode length*.—An average of 1 cm.

*Branching habit*.—Well branched, an average of 8 main stems growing from base of plant per stem 20 cm in length.

Foliage description:

*Leaf shape*.—Lanceolate to linear.

*Leaf division*.—Simple.

*Leaf base*.—Truncate to cuneate.

*Leaf apex*.—Acute.

*Leaf venation*.—Pinnate, inconspicuous, matches leaf color on upper and lower surfaces.

*Leaf margins*.—Entire.

*Leaf attachment*.—Sessile.

*Leaf arrangement*.—Opposite and basal rosettes.

*Leaf surface*.—Smooth, shiny, margins sparsely covered with fine hairs an average of 1 mm in length and match leaf color.

*Leaf color*.—Upper and lower surface; 137A, base 138C.

*Leaf size*.—An average of 1.5 cm in length and 3 mm in width.

*Leaf quantity*.—An average of 19 basal rosettes per main stem, an average of 139 leaves per main stem on a stem 20 cm in length.

*Leaf fragrance*.—Fresh grass-like scent.

Flower description:

*Inflorescence type*.—A few-flowered cyme on the terminus of the lateral branches.

*Lastingness of inflorescence*.—About 3 to 4 weeks from the opening of the first flower to senescence of last flower, individual flower lasts about 5 days.

*Inflorescence size*.—An average of 5 cm in height and 6 cm in diameter.

*Flower fragrance*.—Slight pleasant fragrance.

*Flower number*.—An average of 3 per inflorescence.

*Flower aspect*.—Upright and outward from stem, upright from pedicel.

*Flower bud*.—Spatulate in shape with broadly acute apex, an average of 1.6 cm in length and 3 mm in width, color; N78B to N78C.

*Flower form*.—Salverform.

*Flower size*.—An average of 1.6 cm in height and 2.5 cm in diameter.

*Corolla tube*.—An average of 1.5 cm in length and 3 mm in width (apex), color a blend of 75A and 75D both surfaces, glabrous and satiny surface on both surfaces.

*Corolla lobes*.—5, obcordate in shape, held nearly horizontally when fully open, slightly overlapping near base, slightly wavy in aspect, an average of 1 cm in length and 6 mm in width, apex rounded and bi-lobed, base broadly cuneate and fused to tube, entire margins, color upper surface when opening and fully open; N78B and blending into eye 72A and N92A, color lower surface when opening and fully open; N78C to N78D with a small striations of N77A at base, glabrous and slightly satiny on upper and lower surfaces.

*Calyx*.—Campanulate in form, comprised of fused sepals with linear shaped sepal tips free, an average of 1 cm in length and 5 mm in width.

*Sepals*.—5, primarily fused with free tips, linear in shape, entire margins, fused base (about 50% to 75%), aristulate apex, an average of 1 cm in length and 2 mm in width, color on inner and outer surface 138A, inner surface; glabrous, smooth, and shiny, outer surface; moderately covered with wooly hairs about 0.5 mm in length, matches surface color.

*Peduncles*.—Rounded in shape, an average of 2 cm in length and 1 mm in width, held upright to outward, moderate in strength, color; 182B, surface satiny and densely covered with wooly hairs less than 0.5 mm in length and match surface color.

*Pedicels*.—Rounded in shape, an average of 7 cm in length and 1 mm in width, held at an average angle of 15° to peduncle, moderate in strength, color 182B, surface satiny and densely covered with wooly hairs less than 0.5 mm in length and match surface color.

Reproductive organs:

*Gynoecium*.—1 pistil, stigma; tri-lobed, each lobe is about 1 mm in length and N144A in color, style; about 1.3 cm in length and 0.3 mm in width, N144A in color, ovary; superior, ovate to oval in shape, about 2 mm in length and width, 141C in color.

*Androcoecium*.—5 stamens, anthers; dorsifixed, oblong in shape, 1.3 mm in length, and 23A in color, filaments; adnate to petals, an average of 5 mm in length and 155C in color, pollen; abundant in quantity and 23A in color.

*Seeds*.—None observed.

It is claimed:

1. A new and distinct cultivar of *Phlox* plant named 'Early Bird' as herein illustrated and described.

* * * * *